(12) United States Patent
Takemura et al.

(10) Patent No.: US 6,191,129 B1
(45) Date of Patent: Feb. 20, 2001

(54) BICYCLIC AMINE DERIVATIVE

(75) Inventors: Makoto Takemura; Hisashi Takahashi; Katsuhiro Kawakami, all of Tokyo (JP)

(73) Assignee: Daiichi Pharmaceutical Co., Ltd., Tokyo (JP)

( * ) Notice: Under 35 U.S.C. 154(b), the term of this patent shall be extended for 0 days.

(21) Appl. No.: 09/147,893

(22) PCT Filed: Sep. 26, 1997

(86) PCT No.: PCT/JP97/03440

§ 371 Date: Mar. 18, 1999

§ 102(e) Date: Mar. 18, 1999

(87) PCT Pub. No.: WO98/13370

PCT Pub. Date: Apr. 2, 1998

(30) Foreign Application Priority Data

Sep. 27, 1996 (JP) .................................... 8/255202

(51) Int. Cl.[7] ..................... A61K 31/5383; C07D 265/38
(52) U.S. Cl. ................... 514/230.2; 514/230.2; 544/101; 544/102
(58) Field of Search .................. 544/101, 102; 514/230.2

(56) References Cited

U.S. PATENT DOCUMENTS 5,266,569 * 11/1993 Brighty ..................... 514/229.8

FOREIGN PATENT DOCUMENTS

| 0413455A2 | * 7/1990 | (EP) | ......................... 401/4 |
| 64-56673 | 3/1989 | (JP) . | |
| 96/23782 | 8/1996 | (WO) . | |

* cited by examiner

*Primary Examiner*—Mukund J. Shah
*Assistant Examiner*—Ben Schroeder
(74) *Attorney, Agent, or Firm*—Sughrue, Mion, Zinn, Macpeak & Seas, PLLC

(57) ABSTRACT

A pyridobenzoxazine derivative having a bicyclic amine derivative as its substituent, represented by the formula (I):

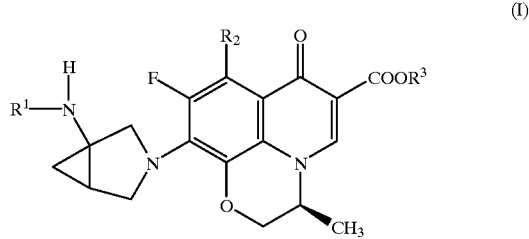

exhibiting antimcrobial activity, and useful in treating infectious diseases and preserving food and agricultural products.

24 Claims, No Drawings

BICYCLIC AMINE DERIVATIVE

TECHNICAL FIELD

This invention relates to a pyridobenzoxazine derivative having 1-amino-3-azabicyclo[3.1.0]hexan-3-yl group as its substituent, which has an excellent antibacterial activity, good pharmacokinetics and high safety, and to a drug, an antibacterial agent and an antibacterial preparation, which contain said compound.

BACKGROUND ART

Since the discovery of Norfloxacin, antibacterial activity and pharmacokinetics of quinolone antibacterial agents have been improved, and many compounds are now used in the clinical field as chemotherapeutic agents which are effective in almost systemic infectious diseases.

In recent years, increasing of bacteria having low sensitivity to quinolone antibacterial agents is becoming a problem in the field of clinics. For example, like the case of *Staphylococcus aureus* (MRSA) which is non-sensitive to β-lactam antibiotics, a case has been increasing in which a bacterium originally resistant to drugs other than quinolone antibacterial agents becomes low-sensitive to quinolone antibacterial agents. In consequence, development of a drug having also the higher efficacy has been called for in the field of clinics.

On the other hand, it has been revealed that quinolone antibacterial agents cause a side effect in which convulsion is induced when a non-steroidal anti-inflammatory drug is simultaneously taken, as well as other side effects such as phototoxicity and the like, so that development of a quinolone antibacterial agent having the higher safety has also been called for in the field.

Quinolonecarboxylic acid derivatives having a substituent derived from 3-azabicyclo[3.1.0]hexylamine, which relates to the present invention, have been disclosed for example in JP-A-64-56673 and JP-A-7-48367 (the term "JP-A" as used herein means an "unexamined published Japanese patent application"). Although these disclose a compound represented by the following formula, they describe only about compounds having quinoline skeleton but do not describe about compounds having pyridobenzoxazine skeleton of the present invention which will be described later.

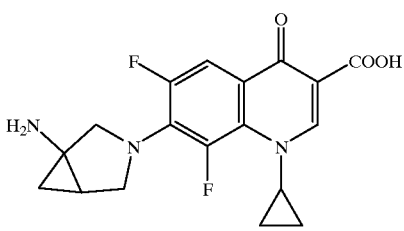

Also, JP-A-3-86875 and JP-A-7-149758 disclose compounds represented by the following formula, but they do not concretely disclose any compound of the present invention.

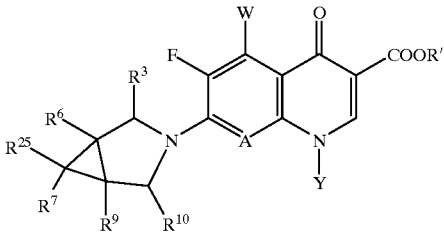

(In the above formula, A, $R^3$, $R^6$, $R^7$, $R^9$, $R^{10}$, $R^{25}$, R', W and Y are various substituents such as an alkyl group. In this connection, definition of the substituents related to the above compound is independent to that of the compound of the present invention.)

In addition, JP-A-3-86875 and JP-A-7-149758 disclose compounds represented by the following formula (A), which have pyridobenzoxazine skeleton. However, though pyridobenzoxazine derivatives having 6-amino-3-azabicyclo [3.1.0]hexan-3-yl group as a substituent at the 10-position are concretely described in these publications, there is no concrete description about pyridobenzoxazine derivatives of the present invention having 1-amino-3-azabicyclo[3.1.0] hexan-3-yl group as a substituent at the 10-position. What is more, nothing is described therein about the excellent pharmacokinetics and safety of the pyridobenzoxazine compounds of the present invention having the 1-amino-3-azabicyclo[3.1.0]hexan-3-yl group as the substituent at the 10-position.

(A)

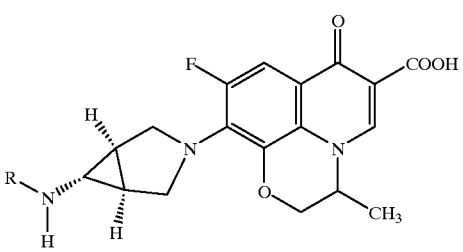

(In the compounds of formula (A), definition of the substituents related to the above compound is independent to that of the compound of the present invention.)

DISCLOSURE OF INVENTION

In view of the above, the inventors of the present invention have conducted intensive studies with the aim of providing a compound which has an excellent antibacterial activity, high efficacy and excellent safety. As a result of the efforts, it was found that a pyridobenzoxazine compound represented by the following formula (I) is superior to a corresponding compound represented by the foregoing formula (A), thereby resulting in the accomplishment of the present invention.

That is, it was found that the compound represented by the formula (I) is possessed of broad and excellent antibacterial activity upon both Gram-negative and Gram-positive bacteria, particularly shows strong antibacterial activity against quinolone-resistant bacteria and also has excellent pharmacokinetics and safety.

A compound represented by formula (I):

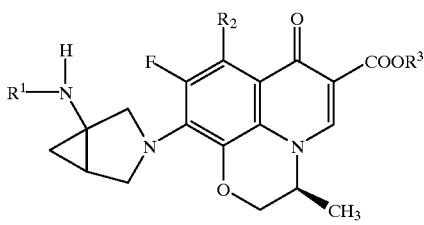

(I)

wherein $R^1$ represents a hydrogen atom or an alkyl group having 1 to 6 carbon atoms, in which said alkyl group may have a substituent selected from the group consisting of a hydroxyl group, a halogen atom, an alkylthio group having 1 to 6 carbon atoms and an alkoxyl group having 1 to 6 carbon atoms;

$R^2$ represents a hydrogen atom or an amino group, in which said amino group may have one or two substituents selected from the group consisting of a formyl group, an alkyl group having 1 to 6 carbon atoms and an acyl group having 2 to 6 carbon atoms; and $R^3$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group, a salt thereof, or a hydrate thereof.

Accordingly, the present invention relates to a compound represented by the aforementioned formula (I), a salt thereof, or a hydrate thereof.

The present invention also relates to the aforementioned compound, a salt thereof, or a hydrate thereof, wherein the compound of formula (I) is a stereochemically pure compound; a compound of formula (I), a salt thereof, or a hydrate thereof, wherein $R^2$ is a hydrogen atom;

10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid (a compound represented by the following formula), an ester thereof, a salt thereof (of carboxylic acid or ester) or a hydrate thereof (of the carboxylic acid, ester, salt of carboxylic acid and salt of ester)

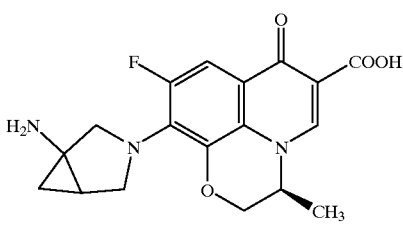

10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof (of carboxylic acid or ester), or a hydrate thereof (of carboxylic acid, ester, salt of carboxylic acid or salt of ester), which comprises a pure isomer;

a compound of formula (I), a salt thereof, or a hydrate thereof, wherein $R^2$ is an amino group;

8-amino-10-(1-amino-3-azabicyclo[3.1.0]hexan-3-yl)-9-fluoro-2,3-dihydro-3-(S)-methyl-7-oxo-7H-pyrido[1,2,3-de]-benzoxazine-6-carboxylic acid (a compound represented by the following formula), an ester thereof, a salt thereof (of carboxylic acid or ester), or a hydrate thereof (of carboxylic acid, ester, salt of carboxylic acid or salt of ester);

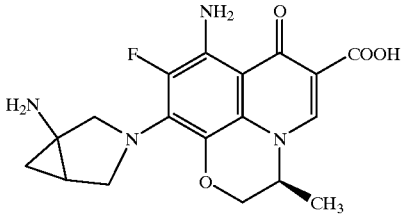

8-amino-10-(1-amino-3-azabicyclo[3.1.0]hexan-3-yl)-9-fluoro-2,3-dihydro-3-(S)-methyl-7-oxo-7H-pyrido[1,2,3-de]-benzoxazine-6-carboxylic acid, an ester thereof, a salt thereof (of carboxylic acid or ester), or a hydrate thereof (of carboxylic acid, ester, salt of carboxylic acid or salt of ester), which comprises a pure isomer;

a pharmaceutical preparation which comprises as an active ingredient the compound represented by formula (I), a salt thereof, or a hydrate thereof;

a pharmaceutical preparation which comprises as an active ingredient the compound represented by formula (I), a salt thereof, or a hydrate thereof, wherein the compound of formula (I) is stereochemically pure compound;

a pharmaceutical preparation which comprises as an active ingredient the compound represented by formula (I), a salt thereof, or a hydrate thereof, wherein the compound of formula (I) is a stereochemically pure compound and $R^2$ is a hydrogen atom;

a pharmaceutical preparation which comprises as an active ingredient 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

a pharmaceutical preparation which comprises as an active ingredient 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

a pharmaceutical preparation which comprises as an active ingredient the compound represented by formula (I), a salt thereof, or a hydrate thereof, wherein the compound of formula (I) is a stereochemically pure compound and $R^2$ is an amino group;

a pharmaceutical preparation which comprises as an active ingredient 8-amino-10-(1-amino-3-azabicyclo[3.1.0] hexan- 3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

a pharmaceutical preparation which comprises as an active ingredient 8-amino-10-(1-amino-3-azabicyclo[3.1.0] hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

an antibacterial agent which comprises as an active ingredient the compound represented by formula (I), a salt thereof, or a hydrate thereof;

an antibacterial agent which comprises as an active ingredient the compound represented by formula (I), a salt thereof, or a hydrate thereof, wherein the compound of formula (I) is a stereochemically pure compound;

an antibacterial agent which comprises as an active ingredient the compound represented by formula (I), a salt thereof, or a hydrate thereof, wherein the compound of formula (I) is a stereochemically pure compound and $R^2$ is a hydrogen atom;

an antibacterial agent which comprises as an active ingredient 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

an antibacterial agent which comprises as an active ingredient 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

an antibacterial agent which comprises as an active ingredient the compound represented by formula (I), a salt thereof, or a hydrate thereof, wherein the compound of formula (I) is a stereochemically pure compound and $R^2$ is an amino group;

an antibacterial agent which comprises as an active ingredient 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

an antibacterial agent which comprises as an active ingredient 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

a method for treating infectious diseases which comprises administering to a patient in need of such treatment an effective amount of the compound represented by formula (I), a salt thereof, or a hydrate thereof;

a method for treating infectious diseases which comprises administering to a patient in need of such treatment an effective amount of the compound represented by formula (I), a salt thereof, or a hydrate thereof, wherein the compound of formula (I) is a stereochemically pure compound;

a method for treating infectious diseases which comprises administering to a patient in need of such treatment an effective amount of the compound represented by formula (I), a salt thereof, or a hydrate thereof, wherein the compound of formula (I) is a stereochemically pure compound and $R_2$ is a hydrogen atom;

a method for treating infectious diseases which comprises administering to a patient in need of such treatment an effective amount of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

a method for treating infectious diseases which comprises administering to a patient in need of such treatment an effective amount of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

a method for treating infectious diseases which comprises administering to a patient in need of such treatment an effective amount of the compound represented by formula (I), a salt thereof, or a hydrate thereof, wherein the compound of formula (I) is a stereochemically pure compound and $R^2$ is an amino group;

a method for treating infectious diseases which comprises administering to a patient in need of such treatment an effective amount of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof;

a method for treating infectious diseases which comprises administering to a patient in need of such treatment an effective amount of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer;

the use of the compound represented by formula (I), a salt thereof, or a hydrate thereof for preparing a pharmaceutical preparation;

the use of the compound represented by formula (I), a salt thereof, or a hydrate thereof for preparing a pharmaceutical preparation, wherein the compound of formula (I) is a stereochemically pure compound;

the use of the compound represented by formula (I), a salt thereof, or a hydrate thereof for preparing a pharmaceutical preparation, wherein the compound of formula (I) is a stereochemically pure compound and $R^2$ is a hydrogen atom;

the use of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof for preparing a pharmaceutical preparation;

the use of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer, for preparing a pharmaceutical preparation;

the use of the compound represented by formula (I), a salt thereof, or a hydrate thereof for preparing a pharmaceutical preparation, wherein the compound of formula (I) is a stereochemically pure compound and $R^2$ is an amino group;

the use of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof for preparing a pharmaceutical preparation;

the use of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer, for preparing a pharmaceutical preparation;

the above mentioned use of the compound represented by formula (I), a salt thereof, or a hydrate thereof, wherein said pharmaceutical preparation is an antibacterial agent;

the use of the compound represented by formula (I), a salt thereof, or a hydrate thereof for treating infectious diseases;

the use of the compound represented by formula (I), a salt thereof, or a hydrate thereof for treating infectious diseases, wherein the compound of formula (I) is a stereochemically pure compound;

the use of the compound represented by formula (I), a salt thereof, or a hydrate thereof for treating infectious diseases, wherein the compound of formula (I) is a stereochemically pure compound and $R^2$ is a hydrogen atom;

the use of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof for treating infectious diseases;

the use of 10-(1-amino-3-azabicyclo[3.1.0]hexan-3-yl)-9-fluoro-2,3-dihydro-3-(S)-methyl-7-oxo-7H-pyrido [1,2,3-de]benzoxazine-6-carboxylic acid, an ester thereof, a salt thereof, or a hydrate thereof, which comprises a pure isomer, for treating infectious diseases;

the use of the compound represented by formula (I), a salt thereof, or a hydrate thereof for treating infectious diseases, wherein the compound of formula (I) is a stereochemically pure compound and $R^2$ is an amino group;

the use of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof for treating infectious diseases; and the use of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof, which comprises a pure isomer, for treating infectious diseases.

Each of the substituents of the compound represented by the formula (I) according to the present invention is described in the following.

The substituent $R^1$ is a hydrogen atom or an alkyl group having 1 to 6 carbon atoms, and the alkyl group may have a substituent selected from the group consisting of a hydroxyl group, a halogen atom, an alkylthio group having 1 to 6 carbon atoms and an alkoxyl group having 1 to 6 carbon atoms.

The alkyl group may be straight or branched having 1 to 6 carbon atoms, and its preferred examples include a methyl group, an ethyl group, a normal propyl group and an isopropyl group. The hydroxyl group-substituted alkyl group having 1 to 6 carbon atoms may be straight or branched, and its preferred examples include a hydroxyethyl group and a hydroxypropyl group.

The substituent $R^2$ is a hydrogen atom or an amino group, and the amino group may have one or two substituents selected from the group consisting of a formyl group, an alkyl group having 1 to 6 carbon atoms and an acyl group having 2 to 6 carbon atoms.

When the substituent $R^2$ is an amino group, it may be protected with a generally used protective group. Typical examples of the protective group include (substituted) alkoxycarbonyl group such as tert-butoxycarbonyl and 2,2,2-trichloroethoxycarbonyl; (substituted) aralkyloxycarbonyl group such as benzyloxycarbonyl, paramethoxybenzyloxycarbonyl and paranitrobenzyloxycarbonyl; (substituted) acyl group such as acetyl, methoxyacetyl, trifluoroacetyl, chloroacetyl, pivaloyl, formyl and benzoyl; (substituted) alkyl group or (substituted) aralkyl group such as tert-butyl, benzyl, paranitrobenzyl, paramethoxybenzyl and triphenylmethyl; (substituted) ether group such as methoxymethyl, tert-butoxymethyl, tetrahydropyranyl and 2,2,2-trichloroethoxymethyl; and substituted silyl group such as trimethylsilyl, isopropyldimethylsilyl, tert-butyldimethylsilyl, tribenzylsilyl and tert-butyldiphenylsilyl (trialkylsilyl group and triaralkylsilyl group, which may be substituted with various substituents). Compounds having substituents which are protected with these substituents are particularly suitable as production intermediates. (In this connection, the term "(substituted)" as used herein means "which may have a substituent".)

The substituent $R^3$ is a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

The compound of the present invention is characterized in that it has a substituent represented by the following formula at the 10-position of its pyridobenzoxazine skeleton and also in that it shows strong antibacterial activity against Gram-negative and Gram-positive bacteria, particularly quinolone-resistant bacteria, and is possessed of both excellent pharmacokinetics and safety. In the substituent of the following formula, the carbon atom (which becomes the 1-position) of the bridge head position to which the amino group is connected is an asymmetric carbon, so that the substituent which can be regarded as an antipode is present, and compounds derived from both of such substituents are included in the present invention.

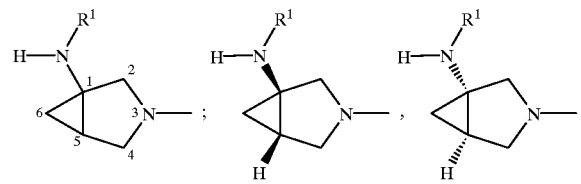

Since diastereomers are present in the compound of formula (I) of the present invention, when a compound of the present invention is administered to human and animals, it is suitable to administer the compound which comprises a pure diastereomer. The term "comprises a pure diastereomer" as used herein means not only a case in which it is completely free from the other diastereomer but also a case in which it is in a chemically pure degree. In other words, it is interpretable that the other diastereomer may be present in such a degree that it does not exert influences upon physical constants and physiological activities of the compound.

Also, the term "stereochemically pure" as used herein means that, when a compound exists in a plurality of isomer forms due to the presence of asymmetric carbon atoms, the compound is comprised of only one of them. The term "pure" in this case can also be considered in the same manner as described above.

The pyridobenzoxazinecarboxylic acid derivative of the present invention may be used either in its free form or as an acid addition salt or a salt of its carboxyl group. Examples of the acid addition salt include inorganic acid salts such as a hydrochloride, a sulfate, a nitrate, a hydrobromide, a hydroiodide or a phosphate; and organic acid salts such as an acetate, a methanesulfonate, a benzenesulfonate, a toluenesulfonate, a citrate, a maleate, a fumarate or a lactate.

The salt of carboxyl group may be either inorganic or organic, and its typical examples include an inorganic salt such as alkali metal salts (e.g., a lithium salt, a sodium salt and a potassium salt), alkaline earth metal salts (e.g., a magnesium salt and a calcium salt) or ammonium salt; and an organic salt such as a triethylamine salt, an N-methylglucamine salt or a tris-(hydroxylmethyl)aminomethane salt.

Also, these free form, acid addition salts and salts of carboxyl group of the pyridobenzoxazinecarboxylic acid derivative may be present as hydrates.

On the other hand, a quinolone derivative whose carboxylic acid moiety is an ester is useful as a synthetic intermediate or a prodrug. For example, alkyl esters, benzyl esters, alkoxyalkyl esters, phenylalkyl esters and phenyl esters are useful as synthetic intermediates.

Also, the ester to be used as a prodrug is an ester which is easily cleaved in the living body to form free carboxylic acid, and its concrete examples include acetoxymethyl ester, pivaloyloxymethyl ester, ethoxycarbonyl ester, choline ester, dimethylaminoethyl ester, 5-indanyl ester, phthalidinyl ester, 5-alkyl-2-oxo-1, 3-dioxol-4-ylmethyl ester and an oxoalkyl ester such as 3-acetoxy-2-oxobutyl ester or the like.

The compound represented by the formula (I) according to the present invention can be produced by various methods, and, in an preferred example of these methods, it can be produced, for example, by allowing a compound represented by formula (III):

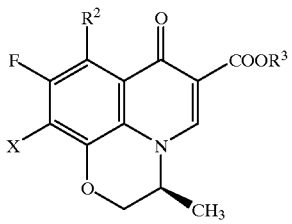

(III)

wherein X is a group which serves as a leaving group, such as a fluorine atom, a chlorine atom, a bromine atom, an alkylsulfonyl group having 1 to 3 carbon atoms, or an arylsulfonyl group such as a benzenesulfonyl group, a toluenesulfonyl group; $R^3$ is the same as defined in the formula (I) as $R^3$ or a boron-containing group represented by formula (IV):

(IV)

wherein $R^4$ and $R^5$ are a fluorine atom or a lower alkylcarbonyloxy group); and $R^2$ is as defined in the formula (I), to react with a compound represented by formula (V):

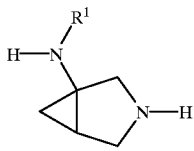

(V)

(wherein $R^1$ is the same as defined in the formula (I) except that $R^1$ may become a protective group Rx of the nitrogen atom, and the protective group Rx is a group generally used in this field, its concrete examples including (substituted) alkoxycarbonyl group such as a tertiary butoxycarbonyl group and a 2,2,2-trichloroethoxycarbonyl group; (substituted) aralkyloxycarbonyl group such as a benzyloxycarbonyl group, a paramethoxybenzyloxycarbonyl group and a paranitrobenzyloxycarbonyl group; (substituted) acyl group such as an acetyl group, a methoxyacetyl group, a trifluoroacetyl group, a chloroacetyl group, a pivaloyl group, a formyl group and a benzoyl group; (substituted) alkyl group or (substituted) aralkyl group such as a tertiary butyl group, a benzyl group, a paranitrobenzyl group, a paramethoxybenzyl group and a triphenylmethyl group; (substituted) ether group such as a methoxymethyl group, a tertiary group, a butoxymethyl group, a tetrahydropyranyl group and a 2,2,2-trichloroethoxymethyl group; and substituted silyl group such as a trimethylsilyl group, an isopropyldimethylsilyl group, a tertiary butyldimethylsilyl group, a tribenzylsilyl group and a tertiary butyldiphenylsilyl group), or an acid addition salt thereof.

When $R^3$ is an alkyl group having 1 to 6 carbon atoms, an alkoxymethyl group having 2 to 7 carbon atoms or a combination of an alkylene group having 1 to 6 carbon atoms and a phenyl group, its conversion into corresponding carboxylic acid is carried out under an ordinary acidic or basic condition for the hydrolysis of carboxylic ester and, if deprotection is necessary, the protective group is removed under an appropriate condition corresponding to the protective group, thereby obtaining the compound of interest represented by the formula (I).

When $R^3$ in the compound of formula (III) is a compound represented by the formula (IV), it can be converted into corresponding carboxylic acid by carrying out a treatment with an acidic or basic compound after substitution reaction with the compound of formula (III) and (V).

The substitution reaction of the compound of formula (III) with the compound of formula (V) can be carried out with or without a solvent. The solvent to be used is not particularly limited, with the proviso that it is inert to the reaction. Typical examples of suitable solvent include dimethyl sulfoxide, pyridine, acetonitrile, ethanol, chloroform, dimethylformamide, dimethylacetamide, N-methylpyrrodidone, tetrahydrofuran, water and 3-methoxybutanol. These solvents may be used alone or as a mixture thereof.

The reaction may be carried out, generally, at a temperature within the range of from room temperature to 200° C., preferably from 25° C. (to 5° C. The reaction time is from 30 minutes to 48 hours, and the reaction is completed generally within the period of from 30 minutes to 2 hours.

It is advantageous to carry out the reaction in the presence of an inorganic or organic base as an acid receptor, for example, inorganic base such as alkali metal carbonates (e.g., lithium carbonate, sodium carbonate and potassium carbonate), alkaline earth metal carbonates (e.g., calcium carbonate and magnesium carbonate), alkali metal hydrogencarbonates (e.g., lithium hydrogencarbonate, sodium hydrogencarbonate and potassium hydrogencarbonate) or alkaline earth hydrogencarbonates (e.g., calcium hydrogencarbonate and magnesium hydrogencarbonate); and organic basic compound such as trialkylamine (e.g., triethylamine, tributylamine and diisopropylethylamine) or a nitrogen-containing heterocyclic compound (e.g., pyridine, dimethylaminopyridine, N-alkylmorpholine, N-alkylpiperidine and 1,8-diazabicycloundecene).

Since the compound of formula (V) has an asymmetric carbon, it may exist in optically active forms, and its racemic compound can be produced in accordance with the method disclosed in JP-A-64-56673. In that case, the compound of formula (I) as the compound of the present invention becomes a mixture of diastereomers. When the compound of the present invention is administered to human or animals, it is suitable to administer a pure diastereomer. The diastereomeric mixture of formula (I) of the present invention can be separated to a pure individual diasteremer by employing a known method.

In this connection, optically active compound of formula (V) can be produced by various methods, and, though not particularly limited, it can be synthesized preferably by the method shown in the Reference Example.

The compound of the present invention has excellent antibacterial activity against Gram-negative and Gram-positive bacteria and shows excellent pharmacokinetics and safety, and, among compounds of the general formula (I), a compound in which $R^2$ is a hydrogen atom or an amino group, or an acid addition salt thereof or a hydrate thereof is suitable, and a compound in which $R^2$ is amino group, or an acid addition salt thereof or a hydrate thereof is particularly suitable. Concrete examples of the suitable compound are as follows.

10-(1-Amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, and 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid.

Since the compound of the present invention has strong antibacterial actions, it can be used as drugs for use in human bodies, animals and fishes or as preservatives of agricultural chemicals and food.

When the compound of the present invention is used as a drug for human bodies, its dosage is within the range of generally from 50 mg to 1 g, preferably from 100 mg to 300 mg, per day per adult.

Its dosage as a drug for animals varies depending on the purpose of its administration (treatment or prevention), kind and size of each animal to be treated, and kind and degree of each infected pathogenic bacteria, but the dosage may be within the range of generally from 1 mg to 200 mg, preferably from 5 mg to 100 mg, per 1 kg body weight per day.

The daily dose may be used once a day or by dividing it into 2 to 4 doses per day. As occasion demands, the daily dose may exceed the aforementioned range.

Since the compound of the present invention is active against a broad range of microorganisms which cause various infectious diseases, it can treat, prevent or alleviate diseases induced by these pathogens.

Concrete examples of bacteria and bacterioid microorganisms on which the compound of the present invention is effective include those which belong to the genus Staphylococcus, *Streptococcus pyogens*, hemolytic streptococci, enterococcus, pneumococcus, those which belong to the genus Peptostreptococcus, *Neisseria gonorrhoeae, Escherichia coli*, those which belong to the genus Citrobacter, those which belong to the genus Shigella, *Klebsiella pneumoniae*, those which belong to the genus Enterobacter, those which belong to the genus Serratia, those which belong to the genus Proteus, *Pseudomonas aeruginosa, Haemophilus influenzae*, those which belong to the genus Acinetobacter, those which belong to the genus Campylobacter, *Chiamydia trachomatis* and the like.

Concrete examples of diseases which are induced by these pathogens include folliculitis, furuncle, carbuncle, erysipelas, phiegmon, lymphangitis, felon, subcutaneous abscess, hidradenitis, acne conglobata, infectious atheroma, perirectal abscess, mastitis, superficial secondary infectious after injury, burn injury, operative wound and the like, pharyngitis, acute bronchitis, tonsillitis, chronic bronchitis, bronchiectasis, diffuse bronchiolitis, secondary infection of chronic respiratory disease, pneumonia, pyelonephritis, cystitis, prostatitis, epididymitis, gonococcal urethritis, non-specific urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, octitis media, sinusitis, periodentitis, pericoronitis, jaw infection, peritonitis, endocarditis, sepsis, meningitis, skin infection and the like.

The inventive compound is also effective against various microorganisms which cause infectious diseases in animals, such as those which belong to the genera Escherichia, Salmonella, Pasteurella, Haemophilus, Bordetella, Staphylococcus, Mycoplasma and the like.

Concrete examples of such diseases include colibacillosis, pullorum disease, avian paratyphoid, avian cholera, infectious coryza, staphylococcosis, Mycoplasma infection and the like in the case of birds; colibacillosis, salmonellosis, pasteurellosis, Haemophilus infection, atrophic rhinitis, exudative epidermis, Mycoplasma infection and the like in the case of pigs; colibacillosis, salmonellosis, hemorrhagic sepsis, Mycoplasma infection, bovine pleuropneumonia, bovine mastitis and the like in the case of cattle; colisepsis, Salmonella infection, hemorrhagic sepsis, uterine empyema, cystitis and the like in the case of dogs; and exudative pleurisy, cystitis, chronic rhinitis, Haemophilus infection, kitten diarrhea, Mycoplasma infection and the like in the case of cats.

The antibacterial preparation which comprises the compound of the present invention can be prepared by selecting appropriate preparation depending on each administration method and employing generally used various preparation method. With regard to the dosage forms of the antibacterial preparation which uses the compound of the present invention as its principal agent, tablets, powders, granules, capsules, solutions, syrups, elixirs, oily or aqueous suspensions and the like can be exemplified as oral preparations.

With regard to injections, a stabilizing agent, an antiseptic agent, a solubilizing agent and the like may be used in the preparation, or a solution which may contain these auxiliary agents may be contained in a container and made into a solid preparation by freeze-drying or the like means to be re-dissolved when used. In addition, a single dose may be contained in a single container or multiple doses maybe contained in the same container.

Also, solutions, suspensions, emulsions, ointments, gels, creams, lotions, sprays and the like can be exemplified as preparations for external use.

Solid preparations may contain pharmaceutically acceptable additives together with the active compound and can be prepared for example by mixing the compound with additives optionally selected from fillers, extenders, binders, disintegrators, solubilization enhancing agents, moistening agents, lubricating agents and the like.

As liquid preparations, solutions, suspensions, emulsions and the like can be exemplified, which may contain a suspending agent, an emulsifying agent and the like as additives.

Examples of the method for administering the compound of the present invention to animals include a method in which it is orally administered directly or by mixing it with feed and the like, a method in which it is made into a solution and then orally administered directly or by mixing it with drinking water, feed and the like, and a method in which it is administered by injection.

With regard to pharmaceutical preparations for use in the administration of the compound of the present invention to animals, it can be made optionally into powders, fine subtilaes, soluble powders, syrups, solutions or injections making use of techniques generally used in this field.

Examples of preparation formulation are shown below.

TABLE 1

| Preparation example 1 (capsules): | |
|---|---|
| compound of Inventive Example 2 | 100.0 mg |
| corn starch | 23.0 mg |
| CMC calcium | 22.5 mg |
| hydroxymethylcellulose | 3.0 mg |
| magnesium stearate | 1.5 mg |
| total | 150.0 mg |

TABLE 1-continued

Preparation example 2 (solutions):

| | |
|---|---|
| compound of Inventive Example 2 | 1–10 g |
| sodium acetate or sodium hydroxide | 0.5–2 g |
| ethyl paraoxybenzoate | 0.1 g |
| purified water | 87.9–98.4 g |
| total | 100 g |

Preparation example 3 (powders for feed mixing use):

| | |
|---|---|
| compound of Inventive Example 2 | 1–10 g |
| corn starch | 98.5–89.5 g |
| soft silicic anhydride | 0.5 g |
| total | 100 g |

BEST MODE FOR CARRYING OUT INVENTION

Examples of the present invention are given below by way of illustration and not byway of limitation. In this connection, the antibacterial activity of each compound of interest was measured in accordance with the standard method specified by the Japan Society of Chemotherapy, with the results shown in Table 2 as MIC values (μg/ml).

[Reference Example A-1]

N-(2-Cyanoethyl)-N-[(1S)-phenylethyl]-3-amino-1,2-propanediol

Glycidol (37 g, 0.5 mol) was added to an ethanol (500 ml) solution of (S)-(−)-phenylethylamine (75 ml, 0.58 mmol), which was cooled in an ice bath, and the mixture was stirred at room temperature for 20 minutes and then heated under reflux for 62 hours. This was mixed with acrylonitrile (40 ml) and again heated under reflux for 45 hours, and then the reaction solution was concentrated. The resulting residue was applied to a silica gel column chromatography to give 121 g (84%) of the title compound from the eluate of 5% methanol-chloroform.

$^1$H-NMR (CDCl$_3$) δ: 1.41–1.48 (3-H, m), 2.39–2.50 (2 H, m), 2.60–3.25 (4 H, m), 3.41–3.46 (1H, m), 3.68–3.78 (2 H, m), 3.93–4.02 (1H, m), 7.27–7.40 (5 H, m).

[Reference Example A-2]

N-(2-Cyanoethyl)-N-[(1S)-phenylethyl]-3-amino-1,2-dibromo-dropane

Triphenylphosphine (57.71 g, 0.22 mol) and carbon tetrabromide (73 g, 0.22 mol) were added to a benzene (400 ml) solution of N-(2-cyanoethyl)-N-[(1S)-phenylethyl]-3-amino-1,2-propanediol (24.8 g, 0.1 mol), and the mixture was heated to 90° C. while stirring. The supernatant solution was collected, the solvent was evaporated and the resulting residue was applied to a silica gel column chromatography. A 38 g (100%) portion of the title compound was obtained from the eluate of n-hexane:ethyl acetate =4:1.

$^1$H-NMR (CDCl$_3$) δ: 1.43–1.46 (3 H, m), 2.35–2.44 (2 H, m), 2.82–2.96 (3 H, m), 3.14–3.27 (1H, m), 3.67–4.15 (4 H, m), 7.27–7.40 (5 H, m).

[Reference Example A-3]

1-Cyano-3-[(1S)-phenylethyl]-3-azabicyclo[3.1.0]hexane

To a toluene (700 ml) solution of N-(2-cyanoethyl)-N-[(1S)-phenylethyl]-3-amino-1,2-dibromopropane (37.4 g, 0.1 mol) was added dropwise 1 M-tetrahydrofuran solution (220 ml, 0.22 mol) of sodium (bistrimethylsilyl)amide while cooling in an ice bath, and the mixture was stirred at the same temperature for 20 minutes. After completion of the reaction, saturated ammonium chloride aqueous solution (100 ml) was added dropwise to the reaction solution which was subsequently warmed to room temperature. The organic layer was collected, washed with saturated brine and then dried over sodium sulfate. The solvent was evaporated and the resulting residue was applied to a silica gel column chromatography. A 7.93 g (37%) portion of the lower polarity title compound (Fr. 1) was obtained from the eluate of n-hexane:ethyl acetate=9:1, and then 7.85 g (36%) of the higher polarity title compound (Fr. 2).

Fr. 1;

$^1$H-NMR (CDCl$_3$) δ: 1.09 (1H, dd, J=4.5, 8.3 Hz), 1.29 (3 H, d, J=6.4 Hz), 1.57 (1H, t, J=4.5 Hz), 1.95–1.99 (1H, m), 2.27 (1H, dd, J=3.9, 9.8 Hz), 2.61 (1H, d, J=8.8 Hz), 2.68 (1 H, d, J=9.8 Hz), 3.33–3.38 (2 H, m), 7.21–7.31 (5 H, m). Fr. 2;

$^1$H-NMR (CDCl$_3$) δ: 1.09 (1H, dd, J=4.9, 8.3 Hz), 1.29 (3 H, d, J=6.4 Hz), 1.55–1.58 (1H, m), 2.04–2.09 (1H, m), 2.35 (1H, d, J=8.8 Hz), 2.53 (1H, dd, J=3.9, 9.3 Hz), 2.86 (1H, d, J=9.3 Hz), 3.18 (1H, d, J=9.3 Hz), 3.32–3.37 (1H, m), 7.21–7.32 (5 H, m).

[Reference Example A-4]

3-[(1S)-Phenylethyl]-3-azabicyclo[3.1.0]hexane-1-carboxylic acid (Fr. 1)

To a methanol (50 ml) solution of 1-cyano-3-[(1S)-phenylethyl]-3-azabicyclo[3.1.0]hexane (Fr. 1; 5.6 g, 26.4 mmol) was added 2 N sodium hydroxide aqueous solution (50 ml), and the mixture was heated under reflux for 30 hours. Methanol was evaporated, and the resulting residue was washed with chloroform (30 ml×2), adjusted to pH 3 with concentrated hydrochloric acid and then extracted with n-butanol (80 ml×3). The extract was dried over sodium sulfate, and then the solvent was evaporated to give 6.11 g (100%) of the crude title compound. This was directly used in the subsequent reaction.

[Reference Example A-5]

3-[(1S)-Phenylethyl]-3-azabicyclo[3.1.0]hexane-1-carboxylic acid (Fr. 2)

Fr. 2 was subjected to the same reaction as in Reference Example A-4.

[Reference Example A-6]

1-Tert-butoxycarbonylamino-3-[(1S)-phenylethyl]-3-azabicyclo-[3.1.0]hexane (Fr. 1)

Diphenylphosphoryl azidate (9.99 g, 34.3 mmol) and triethylamine (4.23 g, 36.9 mmol) were added to atertia-rybutanol (200 ml) solution of 3-[(1S)-phenylethyl]-3-azabicyclo[3.1.0]hexane-1-carboxylic acid (Fr. 1; 6.11 g, 26.4 mmol), and the mixture was heated under reflux for 4 hours. After cooling, the solvent was evaporated and the resulting residue was mixed with 200 ml of ethyl acetate. And the mixture was washed with saturated brine (50 ml×2) and then dried over sodium sulfate. The solvent was evaporated and the resulting residue was applied to a silica gel column chromatography. A 3.19 g (40%) portion of the title compound was obtained from the eluate of n-hexane:ethyl acetate=4:1.

$^1$H-NMR (CDCl$_3$) δ: 0.67–0.71 (1H, m), 1.25–1.31 (4 H, m), 1.45 (9 H, s), 1.60 (1H, brs), 2.30–2.38 (1H, m), 2.51–2.58 (2 H, m), 3.20–3.35 (2 H, m), 4.96 (1H, brs), 7.20–7.29 (5 H, m).

[Reference Example A-7]

1-Tert-butoxycarbonylamino-3-[(1S)-phenylethyl]-3-azabicyclo[3.1.0]hexane (Fr. 2)

Fr. 2 was subjected to the same reaction as in Reference Example A-6.

¹H-NMR (CDCl₃) δ: 0.69–0.71 (1H, m), 1.25 (3 H, d, J=6.4 Hz), 1.39 (9 H, s), 1.50–1.72 (2 H, m), 2.29 (1H, d, J=8.3 Hz), 2.58–2.82 (2 H, m), 3.08–3.15 (1H, m), 3.30–3.38 (1H, m), 4.82 (1H, brs), 7.19–7.37 (5 H, m).

[Reference Example A-8]

1-Tert-butoxycarbonylamino-3-azabicyclo[3.1.0]hexane (Fr. 1)

To an ethanol (50 ml) solution of 1-tert-butoxycarbonylamino- 3-[(1S)-phenylethyl]-3-azabicyclo [3.1.0]hexane (Fr. 1; 3.1 g, 10.26 mmol) was added a 10% palladium-carbon (3 g), and the mixture was subjected to 3 hours of catalytic hydrogenation at 4 atmospheric pressure, while the reaction vessel was heated by an infrared lamp. After removing the catalyst by filtration, the solvent was evaporated to give 2.04 g (100%) of the title compound.

¹H-NMR (CDCl₃) δ: 0.85–1.44 (2 H, m), 1.44 (9 H, s), 1.44–1.70 (1H, m), 2.95–3.34 (4 H, m), 5.08 (1H, brs).

[EXAMPLE 1]

10-(1-Amino-3-azabicyclo[3.1.0]hexan-3-yl)-9-fluoro-2,3-dihydro-3-(S)-methyl-7-oxo-7H-pyrido[1,2,3-de][1,4]-benzoxazine-6-carboxylic acid (isomer A)

To a dimethyl sulfoxide (10 ml) solution of 9,10-difluoro-2,3-dihydro-3-(S)-methyl-7-oxo-7H-pyrido[1,2,3-de][1,4] benzoxazine-6-carboxylic acid BF₂ chelate (900 mg, 2.74 mmol) were added 1-tert-butoxycarbonylamino-3-azabicyclo[3.1.0]hexane (Fr. 1; 800 mg, 4 mmol) and triethylamine (690 mg), and the mixture was stirred at room temperature for 23 hours. After evaporation of triethylamine under a reduced pressure, the thus obtained residue was mixed with water (80 ml) and stirred at room temperature for 30 minutes. The thus precipitated crystals were washed with water, collected by filtration and dissolved in a mixture of methanol:water=4:1 (300 ml), and the resulting solution was mixed with triethylamine (20 ml) and heated under reflux for 3.5 hours. The solvent was evaporated under a reduced pressure, the thus obtained residue was mixed with chloroform (300 ml), washed with 10% citric acid (70 ml×2) and dried over sodium sulfate, and then the solvent was evaporated under a reduced pressure. The thus obtained residue was mixed with concentrated hydrochloric acid (20 ml) and stirred at room temperature for 5 minutes, and the mixture was alkalified by adding 20% sodium hydroxide aqueous solution, then, adjusted to pH 7.2 with concentrated hydrochloric acid and extracted with chloroform (200 ml×3). The extract was dried over sodium sulfate and the solvent was evaporated under a reduced pressure to yield 980 mg of the title compound. By recrystallizing this from 28% ammonia aqueous solution-ethanol, 830 mg (85%) of the title compound was obtained.

¹H-NMR (0.1 N NaOD) δ: 0.71–0.74 (1H, m), 0.79–0.83 (1H, m), 1.37–1.41 (1H, m), 1.45 (3 H, d, J=6.84 Hz), 3.47–3.50 (2 H, m), 3.56–3.67 (2 H, m), 4.26 (1H, d, J=10.74 Hz), 4.43 (1H, d, J=10.74 Hz), 4.50–4.60 (1H, m), 7.38 (1H, d, J=13.67 Hz), 8.30 (1H, s).

Melting point: 212–216° C. (decomp.)

[α]$_D$=−14.45° (c=0.595, 0.1 N NaOH)

Elemental analysis; for $C_{18}H_{18}FN_3O_4$: Calcd.: C, 60.16; H, 5.05; N, 11.69 Found : C, 60.13; H, 5.18; N, 11.45

[EXAMPLE 2]

8-Amino-10-(1-amino-3-azabicyclo[3,1.0]hexan-3-yl)-9-fluoro-2,3-dihydro-3-(S)-methyl-7-oxo-7H-pyrido[1,2,3-de][1,4]-benzoxazine-6-carboxylic acid (isomer A)

To a dimethyl sulfoxide (5 ml) solution of 8-amino-9,10-difluoro-2,3-dihydro-3-(S)-methyl-7-oxo-7H-pyrido[1,2,3-de][1,4]benzoxazine-6-carboxylic acid (200 mg, 0.68 mmol) were added 1-tert-butoxycarbonylamino-3-azabicyclo[3.1.0]hexane (Fr. 1; 270 mg, 1.36 mmol) and triethylamine (1 ml), and the mixture was heated at 100° C. for 24 hours. After evaporation of the solvent under a reduced pressure, the thus obtained residue was mixed with chloroform (50 ml), the resulting solution was washed with 10% citric acid (20 ml×2) and dried over sodium sulfate, and then the solvent was evaporated under a reduced pressure. The thus obtained residue was mixed with concentrated hydrochloric acid (5 ml) and stirred at room temperature for 5 minutes, and the mixture was washed with chloroform (30 ml×3), alkalified by adding 20% sodium hydroxide aqueous solution, then, adjusted to pH 7.2 with concentrated hydrochloric acid and extracted with chloroform (50 ml×3). The extract was dried over sodium sulfate, and the solvent was evaporated under a reduced pressure to yield 201 mg of the crude title compound. By recrystallizing this from 28% ammonia aqueous solution-ethanol, 160 mg (63%) of the title compound was obtained.

¹H-NMR (0.1 N NaOD) δ: 0.65–0.76 (1H, m), 0.78–0.79 (1H, m), 1.33–1.35 (1H, m), 1.40 (3 H, d, J=6.84 Hz), 3.40–3.52 (3 H, m), 3.60–3.65 (1H, m), 3.96 (1H, d, J=10.74 Hz), 4.27 (1H, d, J=10.74 Hz), 4.35–4.39 (1H, m), 8.12 (1H, s)

Melting point: >224° C. (decomp.)

Elemental analysis; for $C_{18}H_{12}N_4O_4 \cdot 0.25H_2O$: Calcd.: C, 57.06; H, 5.19; N, 14.79 Found : C, 56.92; H, 5.27; N, 14.63

TABLE 2

| Bacteria/Compound (Example No.) | 1 | A |
|---|---|---|
| E. coli, NIHJ | ≦0.003 | 0.006 |
| S. flexneli, 2A 5503 | ≦0.003 | 0.013 |
| Pr. vulgaris, 08601 | ≦0.003 | 0.006 |
| Pr. mirabilis, IFO-3849 | 0.025 | 0.05 |
| Ser. marcescens, 10100 | 0.05 | 0.05 |
| Ps. aeruginosa, 32104 | 0.10 | 0.10 |
| Ps. aeruginosa, 32121 | 0.05 | 0.05 |
| S. maltophilia, IID-1275 | 0.10 | 0.39 |
| S. aureus, 209P | 0.006 | 0.025 |
| S. epidermidis, 56500 | 0.025 | 0.10 |
| Str. pyogenes, G-36 | 0.05 | 0.20 |
| Str. faecalis, ATCC-19433 | 0.10 | 0.20 |
| S. aureus, 870307 | 0.20 | 1.56 |
| S. pneumoniae, J24 | 0.025 | 0.20 |

| Bacteria/Compound | 2 | B |
|---|---|---|
| E. coli, NIHJ | ≦0.003 | ≦0.003 |
| S. flexneli, 2A 5503 | ≦0.003 | 0.013 |
| Pr. vulgaris, 08601 | 0.013 | 0.025 |
| Pr. mirabilis, IFO-3849 | 0.05 | 0.10 |
| Ser. marcescens, 10100 | 0.10 | 0.05 |
| Ps. aeruginosa, 32104 | 0.20 | 0.10 |
| Ps. aeruginosa, 32121 | 0.10 | 0.05 |
| S. maltophilia, IID-1275 | 0.05 | 0.20 |
| S. aureus, 209P | ≦0.003 | 0.006 |
| S. epidermidis, 56500 | 0.013 | 0.05 |
| Str. pyogenes, G-36 | 0.10 | 0.20 |
| Str. faecalis, ATCC-19433 | 0.10 | 0.10 |
| S. aureus, 870307 | 0.10 | 0.78 |
| S. pneumoniae, J24 | 0.025 | 0.10 |

Note: Each of the compounds A and B has 6-amino-azabicyclo-[3.1.0] hexan-3-3-yl group at the 10-position, and other substituents than this position of the compound A are the same as those of the compound 1, and those of the compound B with those of the compound 2.

INDUSTRIAL APPLICABILITY

Thus, as has been described in the foregoing, the compound of the present invention is possessed of excellent antibacterial action against a broad range of Gram-negative and Gram-positive bacteria, showing strong antibacterial activity particularly against Gram-positive bacteria, most particularly against quinolone-resistant bacteria. In addition to this, the compound of the present invention is possessed of both excellent pharmacokinetics and high safety, so that it is excellent as an antibacterial compound. Because of the aforementioned excellent properties, the compound of this invention is useful as an antibacterial agent for use in the treatment of infectious diseases and can be used effectively for the preparation of drugs.

What is claimed is:

1. A compound represented by formula (I), a salt thereof, or a hydrate thereof:

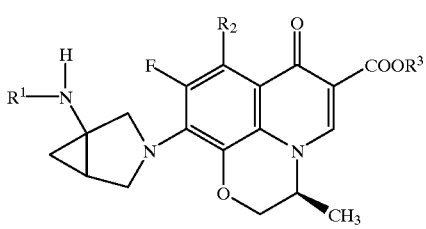

wherein
R¹ represents a hydrogen atom or an alkyl group having 1 to 6 carbon atoms, in which said alkyl group may have a substituent selected from the group consisting of a hydroxyl group, a halogen atom, an alkylthio group having 1 to 6 carbon atoms and an alkoxyl group having 1 to 6 carbon atoms;
R² represents a hydrogen atom or an amino group, in which said amino group may have one or two substituents selected from the group consisting of a formyl group, an alkyl group having 1 to 6 carbon atoms and an acyl group having 2 to 6 carbon atoms; and
R³ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

2. The compound according to claim 1, a salt thereof, or a hydrate thereof, wherein the compound of formula (I) is a stereochemically pure compound.

3. The compound according to claim 1 or 2, a salt thereof, or a hydrate thereof, wherein R² in the formula (I) is a hydrogen atom.

4. 10-(1-Amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

5. A pure stereoisomer of 10-(1-Amino-3-azabicyclo[3.1.0]hexan-3-yl)-9-fluoro-2,3-dihydro-3-(S)-methyl--7-oxo-7H-pyrido[1,2,3-de]benzoxazine-6-carboxylic acid, an ester thereof, a salt thereof, or a hydrate thereof.

6. The compound according to claim 1 or 2, a salt thereof, or a hydrate thereof, wherein R² in the formula (I) is an amino group.

7. 8-Amino-10-(1-amino-3--azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

8. A pure stereoisomer of 8-Amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

9. A pharmaceutical composition for an antibacterial which comprises as an active ingredient an antibacterially effective amount of a compound represented by formula (I), a salt thereof, or a hydrate thereof:

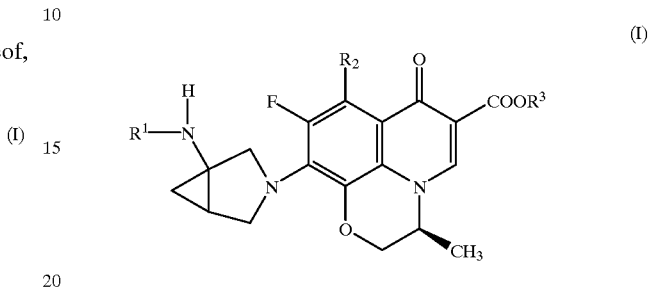

wherein,
R¹ represents a hydrogen atom or an alkyl group having 1 to 6 carbon atoms, in which said alkyl group may have a substituent selected from the group consisting of a hydroxyl group, a halogen atom, an alkylthio group having 1 to 6 carbon atoms and an alkoxyl group having 1 to 6 carbon atoms;
R² represents a hydrogen atom or an amino group, in which said amino group may have one or two substituents selected from the group consisting of a formyl group, an alkyl group having 1 to 6 carbon atoms and an acyl group having 2 to 6 carbon atoms; and
R³ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group, and a pharmaceutically acceptable carrier.

10. The pharmaceutical composition according to claim 9, wherein the compound of formula (I) is a stereochemically pure compound.

11. The pharmaceutical composition according to claim 9 or 10, wherein the compound of formula (I) is a stereochemically pure compound and R² in the formula (I) is a hydrogen atom.

12. A pharmaceutical composition for an antibacterial which comprises as an active ingredient an antibacterially effective amount of 10-(1-amino-3-azabicyclo[3.1.0]hexane-3-yl)-9-flouro-2,3-dihydro-3-(S)-methyl-7-oxo-7H-pyrido[1,2,3-de]benzoxazine-6-carboxylic acid, an ester thereof, a salt thereof, or a hydrate thereof and a pharmaceutically acceptable carrier.

13. A pharmaceutical composition for an antibacterial which comprises as an active ingredient an antibacterially effective amount of a pure stereoisomer of 10-(1-amino-3-azabicyclo[3.1.0]hexane-3-yl)-9-flouro-2,3-dihydro-3-(S)-methyl-7-oxo-7H-pyrido[1,2,3-de]benzoxazine-6-carboxylic acid, an ester thereof, a salt thereof, or a hydrate thereof, and a pharmaceutically acceptable carrier.

14. The pharmaceutical composition according to claim 9 or 10, wherein the compound of formula (I) is a stereochemically pure compound and R² in the formula (I) is an amino group.

15. A pharmaceutical composition for an antibacterial which comprises as an active ingredient an antibacterially effective amount of 8-amino-10-(1-amino-3-azabicyclo[3.1.0]hexane-3 -yl)-9-flouro-2,3-dihydro-3-(S)-methyl-7-oxo-7H-pyrido[1,2,3-de]benzoxazine-6-carboxylic acid, an ester thereof, a salt thereof, or a hydrate thereof and a pharmaceutically acceptable carrier.

16. A pharmaceutical composition for an antibacterial which comprises as an active ingredient an antibacterially effective amount of a pure stereoisomer of 8-amino-10-(1-amino-3-azabicyclo[3.1.0]hexane-3-yl)-9-flouro-2,3-dihydro-3-(S)-methyl-7-oxo-7H-pyrido [1,2,3-de]benzoxazine-6-carboxylic acid, an ester thereof, a salt thereof, or a hydrate thereof, and a pharmaceutically acceptable carrier.

17. A method for treating infectious diseases which comprises administering to a patient in need of such treatment an effective amount of a compound represented by formula (I), a salt thereof, or a hydrate thereof:

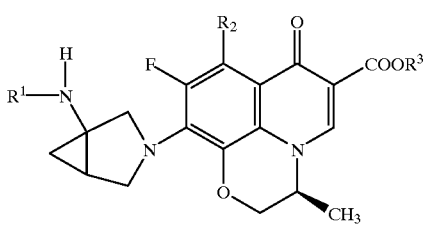

(I)

wherein
$R^1$ represents a hydrogen atom or an alkyl group having 1 to 6 carbon atoms, in which said alkyl group may have a substituent selected from the group consisting of a hydroxyl group, a halogen atom, an alkylthio group having 1 to 6 carbon atoms and an alkoxyl group having 1 to 6 carbon atoms;

$R^2$ represents a hydrogen atom or an amino group, in which said amino group may have one or two substituents selected from the group consisting of a formyl group, an alkyl group having 1 to 6 carbon atoms and an acyl group having 2 to 6 carbon atoms; and $R^3$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

18. The method according to claim 17, wherein the compound of formula (I) is a stereochemically pure compound.

19. The method according to claim 17 or 18, wherein the compound of formula (I) is a stereochemically pure compound and $R^2$ in the formula (I) is a hydrogen atom.

20. A method for treating infectious diseases which comprises administering to a patient in need of such treatment an effective amount of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

21. A method for treating infectious diseases which comprises administering to a patient in need of a pure stereoisomer such treatment an effective amount of 10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

22. The method according to claim 17 or 18, wherein the compound of formula (I) is a stereochemically pure compound and $R^2$ in the formula (I) is an amino group.

23. A method for treating infectious diseases which comprises administering to a patient in need of such treatment an effective amount of 8-amino-10-(1-amino-3-azabicyclo[3.1.0]hexan-3-yl)-9-fluoro-2,3-dihydro-3-(S)-methyl-7-oxo-7H-pyrido[1,2,3-de]benzoxazine-6-carboxylic acid, an ester thereof, a salt thereof, or a hydrate thereof.

24. A method for treating infectious diseases which comprises administering to a patient in need of such treatment an effective amount of a pure stereoisomer 8-amino-10-(1-amino-3-azabicyclo[3.1.0]hexan-3-yl)-9-fluoro-2,3-dihydro-3-(S)-methyl-7-oxo-7H-pyrido[1,2, 3-de]benzoxazine-6-carboxylic acid, an ester thereof, a salt thereof, or a hydrate thereof.

* * * * *